Figure 1:
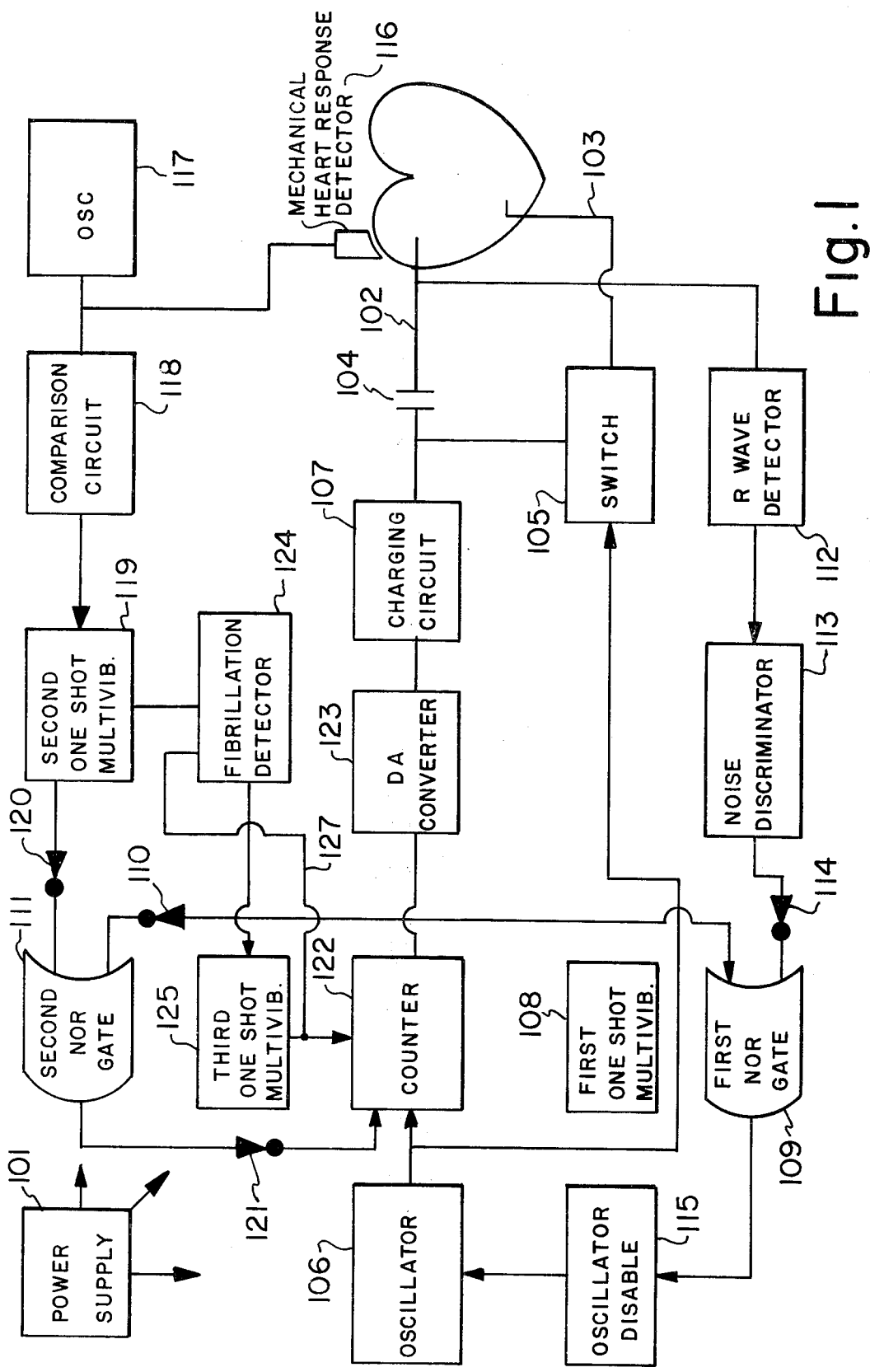

United States Patent [19]

Rizk

[11] 4,114,628
[45] Sep. 19, 1978

[54] DEMAND PACEMAKER WITH SELF-ADJUSTING THRESHOLD AND DEFIBRILLATING FEATURE

[76] Inventor: Nabil I. Rizk, 518 S. Graham St., Apt. 2, Pittsburgh, Pa. 15232

[21] Appl. No.: 801,803

[22] Filed: May 31, 1977

[51] Int. Cl.$^2$ .............................................. S61N 1/36
[52] U.S. Cl. ........................ 128/419 PG; 128/419 D; 128/419 PT
[58] Field of Search ...... 128/419 D, 419 PG, 419 PT

[56] References Cited

U.S. PATENT DOCUMENTS

| | | | |
|---|---|---|---|
| 3,618,615 | 11/1971 | Greatbatch | 128/419 PG |
| 3,638,656 | 2/1972 | Grandjean et al. | 128/419 PG |
| 3,716,059 | 2/1973 | Welborn et al. | 128/419 D |
| 3,805,795 | 4/1974 | Denniston et al. | 128/419 D |
| 3,865,119 | 2/1975 | Svensson et al. | 128/419 PT |
| 3,920,024 | 11/1975 | Bowers | 128/419 PG |
| 3,949,758 | 4/1976 | Jirak | 128/419 PG |
| 4,041,953 | 8/1977 | Anderson et al. | 128/419 PG |

FOREIGN PATENT DOCUMENTS 1,467,344  3/1977  United Kingdom ................ 128/419 D

*Primary Examiner*—William E. Kamm
*Attorney, Agent, or Firm*—Webb, Burden, Robinson & Webb

[57] ABSTRACT

A implantable ventricular stimulating, ventricular sensing, inhibited heart pacer providing electronically generated stimulating pulses of varying energies depending upon the heart response. The frequency of these pulses is set at a selected rate in the absence of a natural heart beat. Stimulating pulses are inhibited once the natural electrical signal corresponding to ventricular pumping rate (R wave rate) exceeds the selected rate. The output circuit comprises an up-down counter in conjunction with a digital-to-analog converter and output amplifer. An electronic oscillator creates pacing pulses to trigger the output circuit, thus producing the stimulating pulses. Each pacing pulse increments the counter and simultaneously initiates a refractory period control circuit. An electromechanical transducer detects mechanical heart response which is gated to the up-down counter during the refractory period to decrement the counter.

8 Claims, 7 Drawing Figures

DEMAND PACEMAKER WITH SELF-ADJUSTING THRESHOLD AND DEFIBRILLATING FEATURE

Since the introduction of rechargeable power supplies, lithium batteries and nuclear energy sources, long term cardiac pacing has been made possible. Available long-term pacemakers are designed to provide pacing pulses during periods when the heart fails to adequately pace itself, that is, to provide pacing pulses when the natural heart beat frequency drops below, say 72 beats per second, which corresponds to a period of 833 milliseconds. Available pacemakers are designed to provide a minimum pulse, say ten milliamps to assure heart operation during the pacing mode. For a reasonably healthy heart, the 10 milliamp pulse is far in excess of that required to stimulate the heart. Such a heart might be paced at two or three milliamps. Nevertheless, the 10 milliamp pulse is used to provide a margin of safety. Unfortunately, with time the sensitivity of the heart to stimulating pulses decreases and for a given pulse the response becomes less. It is also a fact that each pulse has a damaging effect on the heart. The larger the pulse, the greater the damage. Hence, it is desirable to stimulate the heart only when necessary and then only with the minimum size pulse required to provide the desired response.

Applicant provides an automatically adjustable pacemaker that senses heart response during the pacing periods and increases the stimulating pulse energy as required. Hence, the pacemaker after installation will automatically rise to the minimum required pulse and as the heart becomes less sensitive stimulation will stepwise increase. A pacemaker according to this invention during demand periods typically will operate at two or three milliamps and will increase the pulse size, say, six or seven milliamps, as the heart becomes less sensitive. Applicant's pacemaker is also capable of entering a defibrillating mode in which a one shot defibrillation pulse, say 30 milliamps, is automatically applied in the event of a heart stoppage for a prolonged period of time, say 8 seconds.

Briefly, according to this invention, an electrical cardiac pacer circuit includes an output circuit for delivering a stimulating pulse. Preferably, the output circuit comprises an up-down counter in conjunction with a digital-to-analog converter, and amplifier. An oscillator provides a pulse for triggering the output and incrementing the counter. An electromechanical transducer responsive to ventricular contraction produces a pulse which decrements the counter. The energy level of the stimulating pulse corresponds to the count upon the up-down counter; hence, the energy level of the stimulating pulse increases to provide the desired ventricular contraction.

It is a feature of this invention that the decrementing pulse is gated to the counter only during a refractory period following the stimulating pulse. The duration of the refractory period is critical and should be on the order of 250 milliseconds. Typical heart response is within 200 milliseconds of the stimulating pulse. An additional 50 milliseconds is added to the refractory period as a safety precaution. A larger refractory period is not desirable as extraneous heart responses will cause a further decrementing of the up-down counter without a corresponding incrementing pulse.

An electrical circuit responsive to R waves, preferably including a noise suppressor circuit, outputs a signal which disables the oscillator for triggering the output means. This is a standard feature of demand pacemakers.

According to a preferred embodiment of this invention, the pacer circuit includes a defibrillating circuit which, in response to a predetermined number of inadequate responses to stimulating pulses produces an output pulse to the counter to advance it to maximum count. After a defibrillating pulse, the counter automatically returns to the lowest count.

Figure 2A:
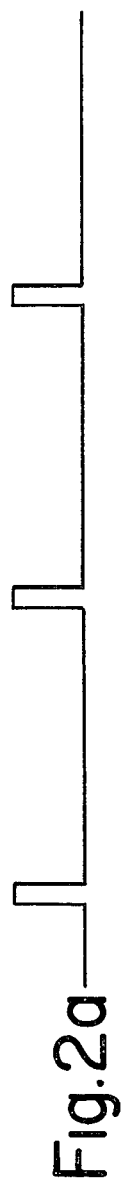
Figure 2B:
Figure 2C:
Figure 2D:
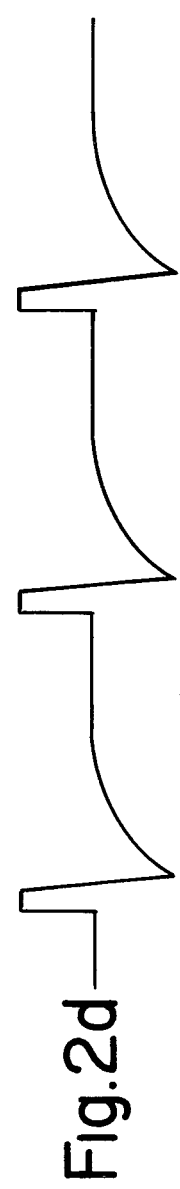
Figure 4:
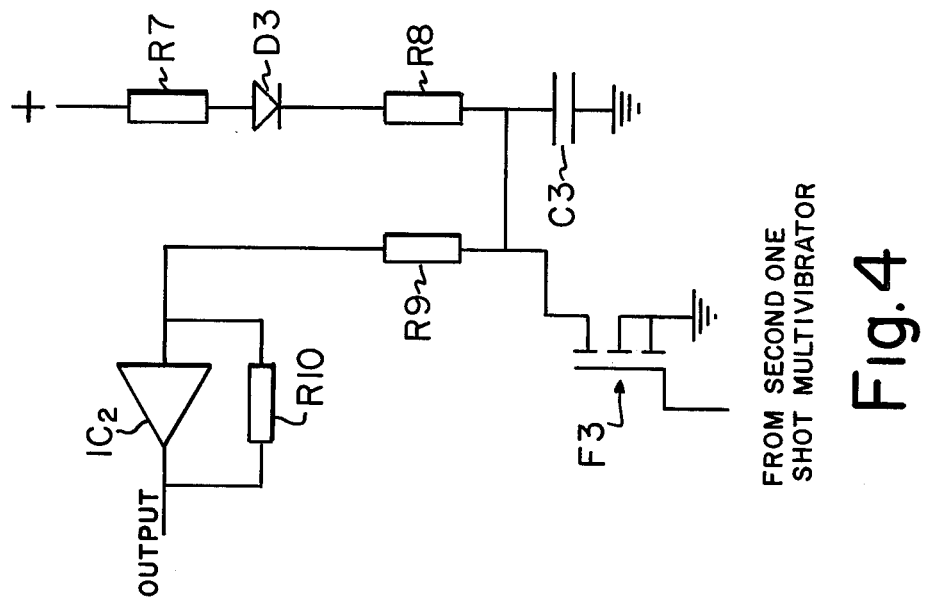
Figure 3:
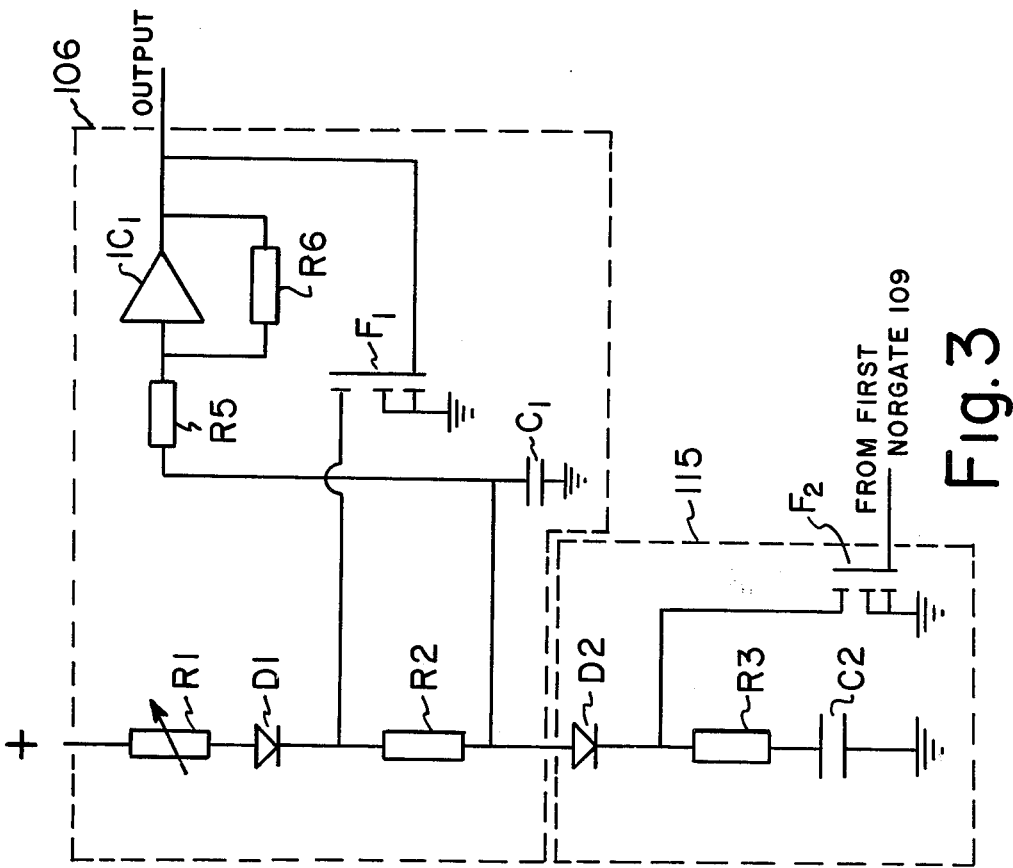

Further features and other objects and advantages of this invention will become clear from the following detailed description made with reference to the drawings, in which FIG. 1 is an overall schematic of a preferred embodiment of this invention, FIGS. 2a through 2d are wave form illustrations used to explain the operation of the circuits set forth in FIG. 1, FIG. 3 is a circuit diagram of a preferred oscillator and oscillator disable circuit according to this invention, and FIG. 4 is a circuit diagram of a preferred fibrillation detection circuit.

Referring now to FIG. 1 which is a block diagram of a pacemaker according to the teachings of this invention, a power supply 101 is shown in the upper left hand corner. It may be a recharageable power supply, lithium batteries or a nuclear energy source. A DC-DC converter will step-up the power supply voltage to a level higher than normal with typical pacemakers. This enables control of the output voltage and thereby the output current and energy by the digital-to-analog converter and amplifier, as explained herein. The power supply provides the electrical supply for all of the blocks in the diagram. This is shown by arrows pointing outwardly therefrom. For simplicity, a connection is not made between the power supply 101 and each other block in the figure to which the power supply is actually connected.

The pacemaker produces a stimulating electrical pulse across electrodes 102 and 103 by discharging capacitor 104 through electronic switch 105. The resulting stimulating pulse waveform is shown schematically in FIG. 2d. Switch 105 is controlled by oscillator 106. Oscillator 106 is designed to output a signal at a frequency somewhat less than the unpaced heart. The oscillator output is shown in FIG. 2a. A charging circuit 107 supplies energy to the capacitor 104 between pulses. The charging circuit 107 is controllable to increase and decreases the amount of energy stored upon the capacitor 104 thereby controlling the intensity of the electrical pulse delivered to the electrodes when the switch 105 is closed (placed in the conducting state).

The output of oscillator 106 is a short pulse relative to the pacing frequency, say about 1 millisecond long. The short oscillator pulse is fed to a first one shot multivibrator circuit 108 where a long pulse (approximately 250 milliseconds) is created. The output of the first one shot multivibrator is applied to the first Nor gate 109 (see FIG. 2b). It is also applied through an inverter 110 (see FIG. 2c) to a second Nor gate 111.

The action of the first and second Nor gates is to pass a signal through one input only when the other input is zero; hence, the second Nor gate 111 can pass a signal during the approximately 250 millisecond period, hereafter the refractory period, immmediately following the oscillator pulse and the first Nor gate can pass a signal during the complementary period preceding the oscillator pulse.

During the complementary period preceding the oscillator pulse an R wave, which is the electrical wave created by ventricular contraction, may be detected by the R wave detector 112 thus producing a signal which is processed by a noise discriminating circuit 113. The output of the noise discriminating circuit is applied to inverter 114 resulting in a positive signal from the first Nor gate 109. This output will activate the oscillator disable circuit 115 causing the next pulse in oscillator 106 to be cancelled. The first Nor gate remains in its signal passing condition (no pulse from the oscillator, hence no pulse from the first multivibrator to place the first Nor gate in the "closed" state). Each time an R wave is detected, the oscillator disable circuit is activated and so long as the heart continues to function without help from the pacemaker, the oscillator disable circuit will keep the oscillator 106 from outputting a signal. Switch 105 remains open and no stimulating pulse is applied to the heart. Should the heart fail to function on its own and thereby fail to output an R wave the signal from the oscillator 106 is applied to the electronic switch 105 thereby delivering a stimulating pulse to the heart. Typically, the oscillator 106 is designed to produce 68 pulses per second corresponding to 890 milliseconds.

A mechanical heart response detector 116 senses the actual mechanical action of the heart in response to the stimulating pulse. It may have associated therewith an oscillator 117 where the detector is of the unprotected high Q inductor type. The output of the detector 116 is fed to a comparison circuit 118 where it is compared to a selected threshold level. If the signal is greater than the threshold, the comparison circuit outputs a signal to the second one shot multivibrator 119 which functions essentially as an antilatch circuit producing a very short output pulse. Hence, if the heart fixes in the contracted position, the output of multivibrator 119 still returns to zero. The output of the antilatch multivibrator 119 is inverted at 120 and applied to the second Nor gate 111. The signal from the comparison circuit 118 will pass the second Nor gate 111 during the refractory period only. The signal passing the second Nor gate is inverted at 121 and applied to a subtraction terminal of the up-down digital counter 122. The output pulses of oscillator 106 are also applied to the add terminal on the up-down digital counter 122. Hence, if after an oscillation pulse and corresponding stimulating pulse, the heart does not respond sufficiently to cause an output of the comparison circuit 118, the counter counts up one. If after an oscillator pulse is followed by a heart response that causes an output from the comparison circuit the net change in the counter 122 is zero. The count upon the counter is applied to digital-to-analog converter 123. The output of the digital-to-analog converter is applied to a controllable charging circuit 107 to adjust the energy stored upon the capacitor 104 between stimulating pulses. The size of the next stimulating pulse is increased automatically to obtain the desired heart response.

The pacemaker according to this invention has an automatic defibrillation feature. The output of one shot multivibrator 119 is passed to fibrillation detector 124. If a preselected number of pulses are not applied to the detector 124, it outputs a signal to the third one shot multivibrator 125 functioning as an antilatch circuit. The third multivibrator 125 outputs a signal to a maximum count terminal of counter 122 thus causing a relatively large quantity of energy to be stored in capacitor 104 for the next pulse. The next pulse is at the defibrillation energy level, say 30 milliamps.

Referring now to FIG. 3, a circuit diagram of a suitable oscillator 106 is set forth. The positive power supply charges capacitor $C_1$ through adjustable resistor $R_1$, diode $D_1$, and resistor $R_2$. The signal on the capacitor $C_1$ is applied to a Schmitt trigger or squaring circuit comprising resistors $R_5$, $R_6$ and operation amplifier $IC_1$. When $C_1$ is charged to a trip level, $IC_1$ outputs a pulse. The output of the Schmitt trigger circuit is feed back to field effect transistor $F_1$ which discharges $C_1$ through resistor $R_2$. The output of the operation amplifier $IC_1$ is a square wave having a pulse the period of which is controlled by the discharge time $C_1R_2$ and a period between pulses controlled by the charging time $C_1 \cdot (R_1 + R_2)$. $R_1$ is adjustable enabling the pacing rate to be adjusted prior to use. FIG. 3 also includes a circuit diagram of a suitable oscillator disable circuit. A signal from first Nor gate 109 causes field effect transistor $F_2$ to discharge capacitor $C_1$ through diode $D_2$ and to discharge capacitor $C_2$ through resistor $R_3$. The quick discharge of capacitor $C_2$ keeps the signal level thereon from throwing operational amplifier $IC_1$ into the outputting condition. Hence closing $F_2$ disables the oscillator 106. Now both capacitors $C_2$ and $C_1$ must charge to the trip level before the oscillator 106 will output a pulse.

FIG. 4 is a circuit diagram of a fibrillation detection circuit. Capacitor $C_3$ is slowly charged through resistors $R_7$ and $R_8$ and diode $D_3$. Capacitor $C_3$ is quickly discharged by field effect transistor $F_3$ every time the second multivibrator outputs a signal (every time the heart beats natural or stimulated). If the heart stops the capacitor $C_3$ will charge to the trip level of Schmitt trigger circuit comprising the resistors $R_{10}$, $R_9$ and operational amplifier $IC_2$. The output of $IC_2$ going positive causes the next stimulating pulse to be at the defibrillation level. The next subsequent pulse is at the lowest possible level as the up-down digital counter automatically resets upon being placed in its maximum count condition.

The above described circuit has two adjustable features: pacing frequency and mechanical response threshold. These may be set by the physician prior to installation by potentiometer adjustments. Another adjustment must be made by the manufacturer. The size of capacitor $C_3$ will control the number of missed responses required to activate the defibrillation mode.

The mechanical heart response detector may be any suitable transducer, which when affixed to the inside or the outside of the heart provides an electrical response proportional to the ventricular contraction. A particularly suitable detector will comprise a moving core inductor, wherein the cores move with the heart. The inductor will be provided with an input signal produced by a suitable oscillator. The output of the inductor will depend upon the position of the core. One transducer of this type referred to herein as the Myocardial or Epicardial type, comprises an unshielded coil (high Q coil formed by winding the coil on a half of a cup type core). The coil is molded and placed in position where a metallic cover can swivel towards the open end of the coil. The coil assembly is attached to the external surface of the heart via a pair of more or less rigid levers. The arrangement is such that with each of the heart systol the cover will swivel closer to the coil, then it will return away from it with the diastole. The cover is, of course, made of a partially magnetic conductive material. Another arrangement referred to herein as an Endocardial type comprises a coil with a movable core positioned inside with a spring load. The coil is positioned inside the ventricule so that the heart walls will push the core inside the coil each time there is a contraction.

OPERATION

When a pacemaker according to this invention is installed the threshold level of comparison circuit 118 and the oscillator frequency are preset. Initially the up-down counter 122 is at the lowest possible count and the output of the charging circuit is such that the capacitor 104 accumulates, say, a 1 milliamp charge between pulses. The capacitor is discharged through the heart by switch 105 in response to a pulse from oscillator 106. But, if during the refractory period mechanical heart response detector 116 and the comparison circuit 118 do not output a decrementing signal the counter counts up one as a result of the application of a pulse from oscillator 106. Thus the output voltage of the charging circuit is increased and the amount of charge stored on a capacitor 104 prior to the next pulse is increased stepwise. The stepwise increase continues until an appropriate response by the heart is detected. One would expect that 2 or 3 milliamps would comprise a satisfactory pulse under normal conditions. As the heart weakens over a period of time, the count may stepwise increase to assure appropriate response. Should the heart stop for, say 10 stepwise increasing stimulating pulses, the fibrillation detector will automatically throw the counter to its maximum count whereby a defibrillating pulse of, say 30 milliamps, is discharged through the heart. Following a defibrillating pulse, the heart should not be stimulated. Since the automatic counter automatically goes to zero after maximum count, the next pulse is at the lowest possible value and, in effect, no stimulation at all. The defibrillation pulse of 30 microamps should restart the heart if it is restartable. The fibrillation detector 124 becomes locked in its outputting condition, but since it is buffered from the counter by a one shot multivibrator it is in effect deactivated unless a mechanical heart response signal passes the comparison circuit in which event the defibrillation detector is reactivated. In an alternate embodiment, the fibrillation circuit automatically resets after a defibrillation pulse whether or not the large stimulating pulse was answered. Reset is caused by feedback from the output of the third one shot multivibrator (See line 127 on FIG. 1).

The R wave detector and the noise discriminator 112 and 113 are well known circuits used in pacemarker circuits. The comparison circuit 118 will typically comprise a differential amplifier. Numerous one shot multivibrators are known in the art and the structure thereof need not be described herein. The embodiment described herein uses analog circuitry. It should be understood that pure digital circuitry can be used to implement parts of this invention explained with analog circuitry herein.

Having thus described my invention with the detail and particularity required by the Patent Laws, what is desired protected by Letters Patent is set forth in the following claims:

1. An implantable, external electrical cardiac pacer circuit comprising output means for delivering a stimulating pulse, oscillator means for triggering the output means, means responsive to electrical signals resulting naturally from a heart beat for disabling the oscillator means, means for detecting mechanical heart response in a refractory period following said stimulating pulse, and adjusting means responsive to the detected mechanical response for controlling the intensity of the next stimulating pulse to provide a desire mechanical response.

2. An electrical cardiac pacer circuit according to claim 1 in which the adjusting means stepwise increases the energy of the stimulating pulse until the desired mechanical response is achieved.

3. An electrical cardiac pacer circuit according to claim 2 in which after a predetermined number of inadequate responses to stimulating pulses, the adjusting means jumps the energy of the next stimulating pulse to a defibrillation level and returns the next succeeding stimulating pulse to the lowest available output level.

4. An electrical cardiac pacer circuit comprising output means for delivering a stimulating pulse including a triggerable switch, oscillator means for producing a triggering pulse at about the natural heart beat rate connected to said triggerable switch, pulse creating means responsive to the trigger pulse for generating a refractory period pulse, means responsive to electrical signals resulting from natural heart beats for disabling the oscillator means, means for detecting a mechanical heart response and comparing said response to a threshold and producing a decrementing signal when the mechanical heart response exceeds the threshold, a digital counter counting up one in response for each trigger pulse and counting down one in response to each decrementing signal, means for passing the output of the detecting and comparing means during the refractory period in response to the refractory period pulse, adjusting means responsive to the count on the digital counter for setting the energy level of the stimulating pulse.

5. An electrical cardiac pacer circuit according to claim 4 further comprising a fibrillation detection circuit, which in response to the failure of the heart to cause a selected number of decrementing signals outputs a pulse that immediately advances the up-down counter to maximum count resulting in the next stimulating pulse being of defibrillating magnitude, said digital counter automatically resetting to zero count.

6. An electric cardiac pacer circuit according to claim 5 further comprising means responsive to a decrementing signal to reset the fibrillation detection circuit.

7. An electric cardiac pacer circuit according to claim 5 further comprising the said means responsive to electrical signals being activated on a period following the refractory period.

8. An electrical cardiac pacer circuit according to claim 5 further comprising an antilatch circuit at the output of the said means for detecting and comparing.

* * * * *